United States Patent [19]

Tindall et al.

[11] Patent Number: 4,585,765

[45] Date of Patent: Apr. 29, 1986

[54] 17β-HYDROXY-17α-METHYL-5α-ANDROSTANO[3,2-C]PYRAZOLE 17-METHYL ETHER

[75] Inventors: Donald J. Tindall; Anthony R. Means, both of Houston, Tex.

[73] Assignee: The Upjohn Company, Kalamazoo, Mich.

[21] Appl. No.: 140,695

[22] Filed: Apr. 16, 1980

Related U.S. Application Data

[63] Continuation of Ser. No. 949,798, Oct. 10, 1978, Pat. No. 4,356,175.

[51] Int. Cl.$^4$ .............................................. A61K 31/58
[52] U.S. Cl. .................................................... 514/172
[58] Field of Search ................................ 424/238, 241; 260/239.5, 239.55

[56] References Cited

U.S. PATENT DOCUMENTS 3,704,295  11/1972  Clinton ............................. 260/239.5
3,980,638   9/1976  Babcock et al. ............... 260/239.55

Primary Examiner—Elbert L. Roberts
Attorney, Agent, or Firm—Bruce Stein

[57] ABSTRACT

17β-Hydroxy-17α-methyl-5α-androstano[3,2-c]pyrazole 17-methyl ether is a very potent reversible male contraceptive which has a very low degree of androgenic side effects. Upon cessation of administration fertility promptly returns.

3 Claims, No Drawings

17β-HYDROXY-17α-METHYL-5α-ANDROSTANO[3,2-C]PYRAZOLE 17-METHYL ETHER

This is a continuation of application Ser. No. 949,798, filed 10-10-78 now U.S. Pat. No. 4,356,175.

BACKGROUND OF THE INVENTION

U.S. Pat. No. 3,704,295 claims (claim 5) 17β-hydroxy-17α-methyl-5α-androstano[3,2-c]pyrazole. The patent further discloses (Column 7) that the steroido[3,2-c]pyrazoles possess pituitary inhibiting properties. Also that "The steroido[3,2-c]pyrazoles of the invention, especially those having a saturated steroid nucleus and hydroxy and lower-alkyl radicals in the 17-position, further possess advantages in being anabolic . . . ". With regards to the steroido[3,2-c]pyrazoles having a double bond in the 4,5-position of the steroid nucleus, the patent states these compounds possess useful pituitary inhibiting activity which is useful in ". . . suppression . . . of reproductive porcesses." No statement is given as to whether the suppression of the reproductive process is in the male and/or female. It is important to note that the compound of the present invention does not have a double bond in the 4,5-position but rather is saturated.

SUMMARY OF THE INVENTION

Disclosed is 17β-hydroxy-17α-methyl-5α-androstano[3,2-c]pyrazole 17-methyl ether.

Also disclosed is a phramceutical composition for oral administration which comprises a contraceptively effective amount of 17β-hydroxy-17α-methyl-5α-androstano[3,2-c]pyrazole 17-methyl ether and appropriate pharmaceutical carriers.

Further disclosed is a method of male contraception which comprises oral administration of a contraceptively effective amount of 17β-hydroxy-17α-methyl-5α-androstano[3,2-c]pyrazole 17-methyl ether to a male mammal post-puberty selected from the group consisting of man, male dog, tom, bull, stallion, ram, boar, male rat and male mouse.

It is preferred that the male mammal be a man.

DETAILED DESCRIPTION OF THE INVENTION

17β-Hydroxy-17α-methyl-5α-androstano[3,2-c]pyrazole 17-methyl ether is prepared by starting with 17β-hydroxy-17α-methyl-5α-androstan-3-one (sold by Steraloids Inc., Wilton, N.H.). The 17-hydroxyl group is methylated after protecting the 3-keto group as a ketal, by reaction with methyl iodide in the presence of silver iodide, diisopropylethlamine and DMF. The pyrazole ring is then synthesized on the A ring of the steroid at $C_2$ and $C_3$ by the procedure of U.S. Pat. No. 3,704,295.

U.S. Pat. No. 3,704,295 states the steroido[3,2-c]pyrazoles of that invention exhibit pituitary inhibiting activity. The patent further states that the steroido[3,2-c]pyrazoles having a double bond in the 4,5-position possess pituitary inhibiting activity which is useful in suppression of the reproduction process. If the assumption is made that the $\Delta^4$-steroido[3,2-c]pyrazoles are contraceptive in the male, because of the pituitary inhibiting properties, these compounds will also exhibit the undesirable side effects of inhibition of pituitary activity, namely a decrease in endogenous androgens which manifests itself in a loss of sex drive, a loss of secondary sex characteristics and a loss of function of accessory male sex organs. Hence, to combat these undesirable side effects concomitant administration of exogenous androgen is necessary.

17β-Hydroxy-17α-methyl-5α-androstano[3,2-c]pyrazole 17-methyl ether, a compound without a 4,5-double bond, causes male contraception with a surprising and unexpected absence of pituitary inhibition.

17β-Hydroxy-17α-methyl-5α-androstano[3,2-c]pyrazole 17-methyl ether, the compositions and methods of the present invention are used to provide reversible contraception for male mammals post puberty which are selected from the group consisting of man, male dog, tom, bull, stallion, ram, boar, male rat, and male mouse.

With regards to the human, there are many instances in which the female cannot take various types of chemical contraceptive agents and does not wish or cannot use various physical contraceptive devices such as IUD (IUCD) or diaphragm. In addition, many womena do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into 2 groups-domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used or even if the particular males are well suited to fertilizing the females it may be desired that they not do so at the present time. The use of 17β-hydroxy-17α-methyl-5α-androstano[3,2-c]pyrazole 17-methyl ether, the compositions and methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the compounds and methods of the present invention. These rodents can be controlled and/or eradicated by decreasing the fertility of these rodents by use of 17β-hydroxy-17α-methyl-5α-androstano[3,2-c]pyrazole 17-methyl ether, the compositions and methods of the present invention. This of course would not eliminate the rodents which are present, but only future rodents which these animals might conceive thereby decreasing future populations of these undesirable animals.

While testosterone and some of its derivatives have been suggested and tried in man as contraceptives in the past, these agents had the distinct disadvantage of typical androgenic side effects which include prostate enlargement, seminal vesicle enlargement, excess and unwanted hair growth and behavioral disturbances. The compound used in the composition and method of treatment of the present invention surprisingly and unexpectedly cause male contraception without causing the typical unwanted androgenic side effects when given in the effective dose range.

17β-Hydroxy-17α-methyl-5α-androstano[3,2-c]pyrazole 17-methyl ether is administered such that the male mammal receives about 0.01 to about 15 mg./kg./day. For a 70 kg. male the amount would be about 0.7 mg. to about 1,050 mg./day.

Since 17β-hydroxy-17α-methyl-5α-androstano[3,2-c]pyrazole 17-methyl ether must be in the blood stream daily to be effective it can be administered daily by tablet, capsule, liquid, treat, bait or veterinary premix incorporated into an animal's feed.

The exact does of 17β-hydroxy-17α-methyl-5α-androstano[3,2-c]pyrazole 17-methyl ether will depend on the weight, age, physical condition and particular patient to be treated.

17β-Hydroxy-17α-methyl-5α-androstano[3,2-c]pyrazole 17-methyl ether is administered in a pharmaceutical composition of following types: tablets, capsules, liquids (elixirs, syrups, suspensions, emulsions), treats, bait, veterinary premix and animal feed.

Various types of tablets and capsules are known to those skilled in the art for formulating pharmaceutical compositions for use by man.

Types of oral tablets are, for example, compressed (including chewable and lozenge), table triturates, enteric-coated,, sugar coated, film-coated, and multiple compressed. Capsules are either hard or soft elastic gelatin.

Pharmaceutically acceptable substances utilized in compressed tablets are binders, lubricants, diluents, disintegrating agents, coloring agents, flavoring agents, flow-inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose high polymer. Multiple compressed tablets are compressed tablets made by more than one compression cycle utilizing the pharmaceutically acceptable substances previously mentioned. Coloring agents are utilized in all the above dosage forms. Flavoring and sweetening agents are utilized in compressed tablets, tablet triturates, sugar coated, multiple compressed and chewable tablets. Flavoring and sweetening agents are especially useful in the formulation of chewable tablets and lozenges.

Examples of binders include glucose solution (25–50%), acacia mucilage (10–20%), gelatin solution (10–20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene lauryl ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 thru 000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil and polysorbate 80.

The individual oral solid pharmaceutical dosage forms, tablets and capsules, are packaged individually (unit-dose) or in quantity (multiple-dose containers), for example, bottles of 50, 100, 500, 1000, or 5000. The amount of 17β-hydroxy-17α-methyl-5α-androstano[3,2-c]pyrazole 17-methyl ether per dosage unit (tablet or capsule) is adjusted so that a tablet or capsule, a fraction or multiple thereof, provides the patient with an effective amount. It is preferred that each tablet or capsule contains 1–250 mg. of 17α-hydroxy-17α-methyl-5α-androstano[3,2-c]pyrazole 17-methyl ether. The exact dose depends on the age, weight, physical condition and the particular patient or animal as is known in the art. Tablets and capsules are given in sufficient number and frequency to obtain the desired pharmacological effect.

The sustained release tablets and capsules provide an effective amount upon ingestion and continue to release a sufficient amount of 17β-hydroxy-17α-methyl-5α-androstano[3,2-c]pyrazole 17-methyl ether to keep the concentration of the active ingredient at an effective level for increased periods of time, for example 12–24 hours.

U.S. Pat. No. 3,150,042 discloses a tablet formulation used to treat dogs, cats and rabbits.

Treats for male dogs and toms are somewhat similar to tablets. They are discrete dosage units which carry an effective amount of 17β-hydroxy-17α-methyl-5α-androstano[3,2-c]pyrazole 17-methyl ether for the particular animal to be treated. It must contain some flavoring agent which makes it especially attractive to the animal, as is known in the art. There are numerous treats on the market for dogs and cats. If 17β-hydroxy-17α-methyl-5α-androstano[3,2-c]pyrazole 17-methyl ether is incorporated the treat is then a pharmaceutical composition within the scope of the present invention.

Many rodenticides are used in the form of bait. Some refer to this as ration, see U.S. Pat. No. 3,659,022. Bait is similar to treat in that it must be attractice to the male rat or male mouse and carry an effective amount of 17β-hydroxy-17α-methyl-5α-androstano[3,2-c]pyrazole 17-methyl ether. Since rats and mice are smaller than dogs and cats, bait will have a smaller amount of the active ingredient. Many commercial baits now in use may be used. 17β-Hydroxy-17α-methyl-5α-androstano[3,2-c]pyrazole 17-methyl ether may be added to, or replace the active ingredient in the commercial baits. The formulation of bait is well known, see U.S. Pat. No. 3,655,889.

Liquid dosage forms can be used in many different ways. A human may take a teaspoonful daily which contains an effective amount of 17β-hydroxy-17α-methyl-5α-androstano[3,2-c]pyrazole 17-methyl ether. For dogs or cats, the liquid may be mixed with their daily feed. The liquid may be formulated as an elixir, syrup, suspension or emulsion as is well known to those skilled in the art. It is preferred that the liquid by a syrup especially when it is to be added to an animal's feed. For example, Cheque ® (mibolerone) is marketed by The Upjohn Company, Kalamazoo, Mich.

Oral administration also utilizes a veterinary premix for the commerical and domesticated animals. This is an advantageous way to administer 17β-hydroxy-17α-methyl-5α-androstano[3,2-c]pyrazole 17-methyl ether to the animal's daily feed as is well known to those skilled in the art. See U.S. Pat. Nos. 3,150,042; 3,251,687; 3,245,797; and 3,482,023.

The feed carriers for domestic and commercial animals comprise in balanced amounts the essential dietary constituents protein, fat, carbohydrate, minerals, and the like. Premixes, for addition to animal feed, contain ingestible bulking agents or diluents which can be dietary constituents, and 17β-hydroxy-17α-methyl-5α-androstano[3,2-c]pyrazole 17-methyl ether in a concentration suited for addition to the animal's feed in amounts calculated on the weight of the animal under treatment.

The animal feed compositions should contain from about 0.0005 to about 0.3% (w/w) of 17β-hydroxy-17α-methyl-5α-androstano[3,2-c]pyrazole 17-methyl ether.

The veterinary premixes contain from about 0.05 to about 5% (w/w) of 17β-hydroxy-17α-methyl-5α-androstano[3,2-c]pyrazole 17-methyl ether. The veterinary premixes are added to the daily feed rations in amounts calculated to provide 17β-hydroxy-17α-methyl-5α-androstano[3,2-c]pyrazole 17-methyl ether in daily dosages of from about 0.01 to about 15 mg./kg.

A dry premix suitable for incorporation into the normal diet of dogs is prepared, for example, from the following types and amounts of ingredients:

| | Kg. |
|---|---|
| PART I | |
| 17β-hydroxy-17α-methyl-5α-androstano[3,2-c]pyrazole 17-methyl ether | 1 |
| Liver protein | 64 |
| Whole liver powder | 60 |
| Fish meal | 200 |
| Terra alba | 24 |
| Dicalcium phosphate | 100 |
| Ferrous gluconate powder | 6½ |
| PART II | |
| Lecithin | 32 |
| Wheat germ oil | 11¼ |
| Brewer's yeast | 200 |

The Part I ingredients are mixed well together. The Part II wheat germ oil is mixed with the warmed lecithin and this mixture is added slowly to the brewer's yeast. The Part II mixture is then blended well with the Part I mixture to give the final product. Each 3.5 gms. (approximately 1 teaspoonful) of the final mixture contains 5 mgs. of the active ingredient. The proper amount of this premix to be added to the animal ration can be calculated from the weight of the animal, the required dosage of active ingredient, and the amount of food consumed per day. In Kirk's Index of Treatment in Small-Animal Practice, published in 1951 by The Williams and Wilkins Company, there is a table on page 713 of food requirements in dogs:

TABLE IV

| Body weight (Kg.) | Grams of food per animal fresh basis (70 percent moisture) per day |
|---|---|
| 1 | 118 |
| 2 | 195 |
| 3 | 262 |
| 4 | 323 |
| 5 | 380 |
| 6 | 433 |
| 7 | 487 |
| 8 | 537 |
| 9 | 483 |
| 10 | 630 |
| 20 | 1040 |
| 30 | 1410 |
| 40 | 1740 |
| 50 | 2043 |

Another table, Number V, is given on page 712 of the same publication.

TABLE V

The following table of approximate quantities of food per day, for maintenance of an adult animal in a well-nourished condition, is one which is considered fairly reliable as a general guide:

| | |
|---|---|
| St. Bernards, mastiffs, great danes | 2.5–4.5 lbs. |
| Collies, retrievers, alsations and similar | 1.5–2.5 lbs. |
| Greyhounds | 1.8–2.5 lbs. |
| Airedales, chows, bulldogs and similar | .8–1.5 lbs. |
| Fox terriers, welsh terriers, scotties, etc. | 8–12 ozs. |
| Pugs, poms, pekingese | 4–8 ozs. |
| Cats | 4–8 ozs. |

From the above tables the amount of premix to be added daily to the food can be calculated. For example, using Table IV, to the 1740 gms. of food per day for a 40 kg. animal, at a daily dosage of 0.5 mg. of active ingredient per kg. of body weight, 4 teaspoonfuls of food supplement are used.

Another example of a verterinary premix is

| | |
|---|---|
| 17β-hydroxy-17α-methyl-5α-androstano[3,2-c]pyrazole 17-methyl ether | 300 gm. |
| Soybean meal | 9700 gm. |
| Chloroform, USP | 1500 ml. |
| | 10,000 gm. |

A chloroform solution of the 17β-hydroxy-17α-methyl-5α-androstano[3,2-c]pyrazole 17-methyl ether is prepared and incorporated gradually and uniformly into the soybean meal. After adequate mixing the whole is vacuum dried to remove any trace of chloroform.

Each gm. of the premix contains 30 mgs. of the active ingredient. The premix is added to the standard ration of feed.

An equally satisfactory premix is prepared by omitting the chloroform and using mineral oil to facilitate the preparation of a uniform premix which is well suited for later incorporation into the animal ration.

Ready-mixed feed may be prepared in the following manner:

| | |
|---|---|
| Commercial dog feed | 100 lbs. |
| 17β-hydroxy-17α-methyl-5α-androstano[3,2-c]pyrazole 17-methyl ether | 400 mgs. |

17β-Hydroxy-17α-methyl-5α-androstano[3,2-c]pyrazole 17-methyl ether is worked into a portion of the feed by careful mixing and the mix is incorporated uniformly into the remaining feed by milling. Each pound of the finished preparation contains 4 mgs. of the steroid providing a total daily dose of 5 mgs. for a 10 kilo dog eating 1¼ lbs. of the feed per day. This daily dose is effective in preventing conception.

The formulation of animal feed and veterinary premix for the remainder of the non-human animals within the scope of the present invention is well within the skill of those skilled in the art.

Regardless of which type of pharmaceutical composition or veterinary premix is used in the methods of treatment of the present invention, a period of pretreatment is required. For 17β-hydroxy-17α-methyl-5α-androstano[3,2-c]pyrazole 17-methyl ether to exert its contraceptive effect, the male animal should be pretreated continuously for a minimum period of 30–90 days depending on the length of the animal's spermatogenic cycle. Following this pretreatment period the male animal may be safely mated with a female animal of the same species at the time of ovulation or estrus without conception taking place. In order to insure continued contraception after the pretreatment period the male animal must maintain a continuous and relatively uniform blood level of the steroid. Therefore, the male animal must continue to take daily doses (tablet, capsule, veterinary premix) of the steriod.

Following cessation of the daily administration of 17β-hydroxy-17α-methyl-5α-androstan[3,2-c]pyrazole 17-methyl ether contraception will be maintained for only a very short period, about 21 days. Gradually over a period of about 90 days the male animal's ability to fertilize the female partner returns to normal.

The definitions and explanations below are for the terms as used throughout the entire patent application including both the specification and the claims.

TLC refers to thin-layer chromatography.

All temperatures are in degrees Centigrade.

SSB refers to an isomeric mixture of hexanes.

DMF refers to dimethylformamide.

NMR refers to nuclear (proton) magnetic resonance spectroscopy, chemical shifts are reported in ppm (δ) downfield from TMS.

MS refers to mass spectroscopy expressed as m/e or mass/charge unit.

When solvent pairs are used, the ratio of solvents are volume/volume (v/v).

Post puberty means a mammal which has a sufficient quantity of healthy normal sperm which can fertilize a female of the same species.

Pharmaceutically acceptable refers to those properties and/or substances which are acceptable to the patient or animal from a pharmacological-toxicological point of view and to the manufacturing pharmaceutical chemist from a physical-chemical point of view regarding composition, formulation, stability, patient acceptance and bioavailability.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

17β-Hydroxy-17α-methyl-5α-androstan-3-one 17-methyl ether

Step A—17β-Hydroxy-17α-methyl-5α-androstan-3-one 3-ethylene ketal

Ethylene glycol (20 ml.) and p-TSA (5 mg.) is added to 17β-hydroxy-17α-methyl-5α-androstan-3-one (sold by Steraloids, Inc., Wilton, N.H., 3.0 g.) in methylene chloride (20 ml.). The mixture is heated on a steam bath until most of the methylene chloride is removed. The remainder of the methylene chloride is removed on a rotary evaporator. The mixture is cooled and a small amount of a sodium bicarbonate solution and water are added and the mixture filtered. The filtered solids are washed and dried to give the title compound, NMR (CDCl$_3$), 0.83, 0.84, 1.20 and 3.29δ.

Step B—17β-Methoxy-17α-methyl-5α-androstan-3-one 3-ethylene ketal

A mixture of 17β-hydroxy-17α-methyl-5α-androstan-3-one 3-ethylene ketal (Step A, 2.0 g.), silver oxide (2.4 g.), methyl iodide (2.4 ml.) and diisopropylethyl amine (3.4 ml.) and DMF (20 ml.) is stirred at 5° for 2 days. Diethyl ether is added and the mixture filtered to remove the inorganic precipitate. The precipitate is washed with diethyl ether and the filtrates combined and successively washed with water, dilute hydrochloric acid, water, dilute sodium bicarbonate solution and water. The organic phase is dried over magnesium sulfate and concentrated to give a residue. The residue is recycled thru the same reaction conditions and workup. The crude product is column chromatographed over silica gel using gradient elution, ethyl acetate-SSB (5:95) and ethyl acetate:SSB (25:75). The appropriate fractions are pooled and concentrated to give the ketal, NMR (CDCl$_3$) 0.82, 0.84, 1.18, 3.22 and 3.92δ.

Step C—17β-Hydroxy-17α-methyl-5α-androstan-3-one 17-methyl ether

The ketal (Step B) is dissolved in acetone (15 ml.) and hydrochloric acid (2N, 2 ml.). The reaction mixture is heated briefly and after 2 hours TLC shows the ketal has been removed. The product is precipitated by the addition of water. The precipitate is recovered by filtration, washed and recrystallized from aqueous acetone to give the title compound, m.p. 130°–131°; MS 318, 303, 286, 271 and 244; NMR (CDCl$_2$) 0.87, 1.02, 1.19 and 3.23δ.

EXAMPLE 2

2-Hydroxymethylene-17β-hydroxy-17α-methyl-5α-androstan-3-one 17-methyl ether

17β-Hydroxy-17α-methyl-5α-androstan-3-one 17-methyl ether (Example 1; 20.7 g.) in benzene (500 ml.) is added to sodium methoxide (prepared by dissolving 15.0 g. of sodium in 250 ml. of absolute methanol, concentrating the mixture and drying the residue for 1 hour at 150°–160° at 15 mm mercury). Ethyl formate (48.8 g.) is added with stirring in a nitrogen atmosphere. The reaction mixture is stirred for 4 hours at 20°–25°, allowed to stand about 15 hours, stirred 2 hours more and poured into water. The benzene layer is separated and the aqueous layer extracted with benzene. Nitrogen is bubbled thru the aqueous layer to remove the remaining benzene and the mixture filtered. Hydrochloric acid (concentrated) and ice are added to the filtrate until the mixture tests acid to Congo red. The product is then extracted with chloroform. The chloroform extracts are washed with water, dried, filtered, and concentrated under reduced pressure to give the title compound.

EXAMPLE 3

17β-Hydroxy-17α-methyl-5α-androstano[3,2-c]pyrazole 17-methyl ether

2-Hydroxymethylene-17β-hydroxy-17α-methyl-5α-androstan-3-one 17-methyl ether (Example 2, 500 mg.) in ethyl alcohol (95%, 40 ml.) is warmed and hyrazine hydrate (160 mg.) is added. The mixture is refluxed 3 hours, concentrated to a volume of about 20 ml. and cooled. The title compound separates, is recovered and washed with ether.

EXAMPLE 4

70 kg. 25 year old man who demonstrates approximately 100 million apparently normal sperm/ml. of ejaculate is treated twice daily with a tablet containing 10 mg. of 17β-hydroxy-17α-methyl-5α-androstano[3,2-c]pyrazole 17-methyl ether for about 100 days, after which time it is found that following sexual intercourse he does not fertilize a fertile female (who has previously delivered a child) at the most fertile time of her cycle. The steroid is continuously administered to the man twice daily and he remains infertile.

EXAMPLE 5

A 80 kg. 22 year old man who demonstrates approximately 90 million apparently normal sperm/ml. of ejaculate is treated with a 200 mg. capsule of 17β-hydroxy-17α-methyl-5α-androstano[3,2-c]pyrazole 17-methyl ether four times daily for 60 days.

After which time it is found that following sexual intercourse he does not fertilize a fertile female (who has previously delivered a child) at the most fertile time of her cycle. The steriod is continuously administered to the man 4 times daily and he remains infertile.

EXAMPLE 6

A 70 kg. 30 year old man who demonstrates approximately 95 million apparently normal sperm/ml. of ejaculate is given one-half teaspoonful/day of an elixir of 17β-hydroxy-17α-methyl-5α-androstano[3,2-c]pyrazole 17-methyl ether (100 mg./ml.). After 60 days it is found that following sexual intercourse he does not fertilize a fertile female (who has previously delivered a child) at the most fertile time of her cycle. Upon continued daily administration of the same amount of the elixir he remains infertile.

EXAMPLE 7

A 60 kg. 26 year old man who is the admitted father of 2 children is given one 50 mg. tablet of 17β-hydroxy-17α-methyl-5α-androstano[3,2-c]pyrazole 17-methyl ether daily. After 60 days it is found that following sexual intercourse he does not fertilize the mother of his 2 children at the most fertile time of her cycle. The steriod is continuously administered daily and he remains infertile.

EXAMPLE 8

A 60 kg. 20 year old man is given one teaspoonful of a suspension of 17β-hydroxy-17α-methyl-5α-androstano[3,2-c]pyrazole 17-methyl ether (100 mg./ml.) daily. After 60 days it is found that following sexual intercourse he does not fertilize a fertile female (who has previously delivered a child) at the most fertile time of her cycle. Upon continuous daily administration the patient remains infertile.

EXAMPLE 9

A 6 kg. tom who has previously sired offspring is given a treat daily containing 20 mg. of 17β-hydroxy-17α-methyl-5α-androstano[3,2-c]pyrazole 17-methyl ether. After 60 days it is found that following sexual intercourse the animal does not fertilize an ovulating female (who has previously delivered kittens) at the time of her estrus. Upon continuous daily administration of the treat to the tom the animal remain infertile. Eighty days following cessation of administration of the treat, the tom upon sexual intercourse fertilized the same ovulating female at the time of her estrus.

EXAMPLE 10

A 10 kg. dog who has previously sired offspring is treated by adding 17β-hydroxy-17α-methyl-5α-androstano[3,2-c]pyrazole 17-methyl ether to its daily food ration as follows, a veterinary premix containing 2% of the active ingredient is added to the animal's daily normal dietary intake such that it provides sufficient quantity of the active material for contraceptive purposes. In the particular case, using a 2% veterinary premix 5 g. of the premix delivers 100 mg. of the contraceptive agent which provides for 10 mg./kg./day. After feeding 60 days on this type of diet it is found that following sexual intercourse the animal does not fertilize an ovulating female (who has previously delivered yound) at the time of her estrus.

In addition to the active ingredient the veterinary premix includes liver protein, whole liver powder, fish meal, terra alba, dicalcium phosphate, ferrous gluconate powder, wheat germ oil, and brewer's yeast in sufficient quantity to provide a verterinary premix containing 2% of the active ingredient.

We claim:

1. A method of male contraception which comprises oral administration of a contraceptively effective amount of 17β-hydroxy-17α-methyl5α-androstano[3,2-c]pyrazole 17-methyl ether to a male mammal post puberty selected from the group consisting of man, male dog, tom, bull, stallion, ram, boar, male rat and male mouse.

2. A method of male contraception according to claim 1 where the male mammal is a man.

3. A method of male contraception according to claim 1 where the contraceptively effective amount is from about 0.01 to about 15 mg./kg./day.

* * * * *